US005958434A

United States Patent [19]
Simon et al.

[11] Patent Number: 5,958,434
[45] Date of Patent: *Sep. 28, 1999

[54] STABLE GELLED WATER IN OIL EMULSION AND ITS USE IN THE COSMETIC, DERMATOLOGICAL, VETERINARY AND/OR FARM PRODUCE FIELDS

[75] Inventors: Pascal Simon, Vitry Sur Seine, France; Didier Gagnebien, Westfield, N.J.

[73] Assignee: L'Oreal, Paris, France

[ * ] Notice: This patent is subject to a terminal disclaimer.

[21] Appl. No.: 08/812,703

[22] Filed: Mar. 6, 1997

[30] Foreign Application Priority Data

Mar. 12, 1996 [FR] France ................... 96-03095

[51] Int. Cl.$^6$ ...................... A61K 7/48
[52] U.S. Cl. ............ 424/401; 424/59; 424/78.02; 514/845; 514/844; 514/846; 514/937
[58] Field of Search ............ 424/401, 59, 78.02; 514/844, 846, 845, 937

[56] References Cited

U.S. PATENT DOCUMENTS 5,186,928 2/1993 Birtwistle ................... 424/59
5,518,647 5/1996 Zocchi ................... 252/174.17

FOREIGN PATENT DOCUMENTS 0281360 7/1988 European Pat. Off. .
0-281 360 A1 9/1988 European Pat. Off. .
0-682 936 A1 11/1995 European Pat. Off. .

OTHER PUBLICATIONS

Research disclosure by Hercules Incorporated, Oct. 1995.
Clarke et al,, *World Patent Index* (abstract), 96–207276, May, 1996.
Srcic et al., *Chemical Abstracts*, vol. 97, #11692, 1981.
Majewicz et al., "Oil–Based Cosmetic and Therapeutic Compositions Containing Ethylguar", Research Disclosure, No. 37807, Oct. 1995, p. 642 XP002018143.

*Primary Examiner*—Jyothsna Venkat
*Attorney, Agent, or Firm*—Oblon, Spivak, McClelland, Maier & Neustadt, P.C.

[57] ABSTRACT

The present invention relates to a stable fluid water-in-oil emulsion, in particular a topical emulsion, comprising, as gelling agent, a polysaccharide alkyl ether formed from units containing at least two different monosaccharide rings, each unit containing at least one hydroxyl group substituted by a saturated hydrocarbon alkyl chain. The polysaccharide alkyl ether preferably has a weight average molecular weight greater than 200,000 and preferably is a guar gum alkyl ether having a degree of substitution of approximately 2 to 3. The emulsion obtained is stable, even in the absence of an electrolyte or a fatty substance commonly used to stabilize water-in-oil emulsions. It can in particular contain an active ingredient sensitive to electrolytes. The emulsion according to the invention can be used in particular in the cosmetics and/or dermatological fields.

16 Claims, No Drawings

STABLE GELLED WATER IN OIL EMULSION AND ITS USE IN THE COSMETIC, DERMATOLOGICAL, VETERINARY AND/OR FARM PRODUCE FIELDS

BACKGROUND OF THE INVENTION

1. Field of the Invention

The present invention relates to a stable fluid water-in-oil emulsion and to its use in the cosmetics, dermatological, veterinary and/or farm-produce fields. It can be provided in the form of a white or colored cream intended in particular for caring for the skin, make up for the skin, mucous membranes or for protection from the sun of the skin or mucous membranes, as well as for the preparation of a cream intended for the treatment of diseases of the skin and/or mucous membranes.

2. Discussion of the Related Art

In the cosmetics field, it is common to use creams composed of a water-in-oil (W/O) emulsion containing an aqueous phase dispersed in an oil phase. These emulsions contain a continuous oil phase and, thus, make it possible to form a lipid film on the surface of the skin which prevents transepidermal water loss and protects the skin from external attacks. These emulsions are particularly appropriate for protecting and nourishing the skin and in particular for treating dry skins.

These emulsions frequently present problems of stability, making their manufacture difficult. Various means have consequently been envisaged for overcoming this disadvantage. One means comprises the incorporation in the oil phase of an emulsion of fatty substances which are solid at room temperature, such as waxes or waxy compounds, silicas or modified clays, with the aim of thickening the continuous phase. However, this results in creams being obtained which are often dense and heavy.

Another means of overcoming the instability of W/O emulsions is the incorporation of an inorganic electrolyte, such as magnesium sulphate, which stabilizes the emulsion by the effect of electrostatic repulsion, preventing the phenomena of coalescence of the dispersed water globules. The absence of electrolyte increases the risks of instability of the emulsion, which is often reflected by a phase separation of the two phases. However, the presence of electrolyte can have disadvantages because it transpires that certain compounds which are desirable to use in these emulsions, are incompatible with electrolytes. It is known, for example, that anionic active ingredients form insoluble salts in the presence of inorganic electrolytes and end up precipitating more or less rapidly in the emulsion. Mention may be made, as anionic active ingredient of this type, for example, water-soluble UV screening agents, such as terephthalylidenedicamphorsulphonic acid or 4-benzophenone.

In addition, it is possible to overcome the instability of W/O emulsions by greatly increasing the emulsifier content of these emulsions. It is known, however, that emulsifiers used in a large amount can prove to be irritating to certain types of skin. Moreover, the creams obtained as described above, are often dense and heavy.

For the foregoing reasons, there remains a need for a water-in-oil emulsion which does not exhibit the disadvantages encountered with those known to date, this emulsion being stable even in the presence of an active ingredient sensitive to an electrolyte and/or in the absence of an electrolyte and/or of a solid fatty substance.

SUMMARY OF THE INVENTION

The emulsion according to the invention makes it possible to overcome the above-mentioned problems. In fact, Applicants have found, surprisingly, that it was possible to obtain a water-in-oil emulsion having good cosmetic properties and good stability by using a specific gelling agent.

An object of the present invention is consequently a water-in-oil emulsion containing an oil phase comprising at least one gelling agent, characterized in that the emulsion is fluid and in that the gelling agent is a polysaccharide alkyl ether formed from units containing at least two different monosaccharide rings, each unit containing at least one hydroxyl group substituted by a saturated hydrocarbon alkyl chain.

In particular, an emulsion in accordance with the present invention is stable even if it contains at least one active ingredient sensitive to an electrolyte and/or if it is free from a electrolyte or from solid fatty substance.

Depending on the percentage of gelling agent used, it is possible to obtain an emulsion of more or less fluid texture. Emulsion of fluid texture is understood to mean an emulsion which flows under its own weight and which has a viscosity of approximately 2 to 15 poises, i.e. from 0.2 to 1.5 Pa.s. An emulsion of thick texture according to the prior art has a viscosity of approximately 20 to 80 poises, i.e. from 2 to 8 Pa.s. The emulsion according to the invention has the advantage of being able to be fluid, creamy and comfortable while exhibiting good stability.

A further subject of the invention is consequently the use of a polysaccharide alkyl ether formed from units containing at least two different monosaccharide rings, each unit containing at least one hydroxyl group substituted by a saturated hydrocarbon alkyl chain, for stabilizing a fluid water-in-oil emulsion.

These and other features, aspects and advantages of the present invention will become better understood with reference to the following description and appended claims.

DESCRIPTION OF THE PREFERRED EMBODIMENTS

According to a specific embodiment of the invention, the polysaccharide alkyl ether preferably has a weight average molecular weight greater than 100,000 and more preferably greater than 200,000. Each unit can contain from one to six and preferably from two to four hydroxyl groups substituted by a saturated hydrocarbon alkyl chain.

Saturated hydrocarbon alkyl chain is understood to mean a chain containing from 1 to 24, preferably from 1 to 10 and more preferably from 1 to 5 carbon atoms. In particular, the alkyl chain is chosen from methyl, ethyl, n-propyl, isopropyl, n-butyl, isobutyl, tert-butyl and n-pentyl chains.

The monosaccharide rings are in particular chosen from mannose, galactose, glucose, furanose, rhamnose and arabinose.

According to a preferred embodiment of the invention, the polysaccharide alkyl ether according to the invention is an alkyl ether of a gum and more particularly of a gum which is overall non-ionic, that is to say virtually without ionic groups. Appropriate gums include, but are not limited to guar gum, the unit of which comprises a galactose and a mannose, locust bean gum, the unit of which comprises a galactose and a mannose, karaya gum, which is a complex mixture of rhamnose, galactose and galacturonic acid, or gum tragacanth, which is a complex mixture of arabinose, galactose and galacturonic acid.

According to a preferred embodiment of the invention, the polysaccharide alkyl ether is a derivative of guar gum and more particularly ethylated guar having a degree of substitution of approximately 2 to 3, in particular 2.5, as described in the document RD 95378007 (October 1995), which is incorporated herein by reference.

The emulsion according to the invention can contain, for example, an amount of polysaccharide alkyl ether ranging from 0.1 to 10%, and preferably from 0.5 to 5% by weight, based on the total weight of the emulsion.

The amount of oil which can be introduced into the emulsion can represent from 20% to 80% by weight, based on the total weight of the emulsion.

Oils which can be used in the invention include, but are not limited to, oils of vegetable origin, oils of animal origin, synthetic oils, and in particular fatty esters, and mixtures thereof, as well as mixtures of the above oils with silicone oils, fluorinated oils and/or mineral oils.

The emulsion according to the invention may contain an emulsifier for a W/O emulsion. Emulsifiers which can be used in accordance with the invention include, but are not limited to esters of fatty acids and of glucose, such as methylglucose dioleate, esters of fatty acids and of glycerol, such as glyceryl isostearate, glyceryl oleate and glyceryl ricinoleate, or esters of fatty acids and of sorbitol, such as sorbitan tristearate and sorbitan di- or trioleate, and more generally any emulsifier having an HLB (hydrophile-lipophile balance) of less than 6. The amount of emulsifier can represent from 0.1 to 20% and preferably from 0.2 to 3% by weight, based on the total weight of the emulsion.

The emulsion according to the invention is preferably intended for topical care or treatment. In this case, the emulsion must contain a topically acceptable medium, that is to say compatible with the skin, the mucous membranes, the nails, the scalp or the hair. It finds its application in a large number of cosmetic and/or dermatological treatments of the skin, including the scalp, in particular for caring for or make up of the skin or mucous membranes or for the protection against the sun of the skin or mucous membranes as well as for the preparation of a cream intended for the treatment of diseases of the skin (such as dry skin).

A further object of the present invention is, therefore, a process for treating the skin or mucous membranes, characterized in that an emulsion as defined above is applied on the skin or mucous membrane.

Another subject of the present invention is a process for the cosmetic or dermatological treatment of dry skin, characterized in that an emulsion as defined above is applied to the dry skin in an effective amount.

In a known way, the emulsion of the invention can also contain adjuvants usual in the cosmetics and/or dermatological fields, such as an active ingredient, a preservative, an antioxidant, a complexing agent, a solvent, a fragrance, a filler, a screening agent, a bactericide, an odor absorber, a coloring material or alternatively a lipid vesicle. The amount of these various adjuvants are those conventionally used in the field under consideration and, are preferably, from 0.01 to 20% by weight, based on the total weight of the composition. These adjuvants, depending on their nature, can be introduced in the fatty phase, in the aqueous phase or in a lipid vesicle.

Having generally described this invention, a further understanding can be obtained by reference to certain specific examples which are provided herein for purposes of illustration only and are not intended to be limiting unless otherwise specified.

EXAMPLES

Example 1:
Oil phase:
Methylglucose dioleate 3%
Liquid petrolatum 15%
Sunflower oil 10%
Antioxidant 0.05%
Ethylated guar having a degree of substitution of approximately 2.5 1%
Aqueous phase:
Magnesium sulphate 0.8%
Water remainder based on 100%

The fluid emulsions is stable to temperature cycles (+20° C./−20° C.) and to heat (oven at 45° C.). The texture is supple and oily and very pleasant on spreading.

Comparative Example 1:
Oil phase:
Methylglucose dioleate 3%
Liquid petrolatum 15%
Sunflower oil 10%
Antioxidant 0.05%
Aqueous phase:
Magnesium sulphate 0.8%
Water remainder based on 100%

The emulsion of Comparative Example 1 differs from Example 1 by the absence of gelling agent according to the invention. The emulsion obtained is not stable to temperature cycles and to heat (oven at 45° C.). The emulsion is only stable with at least 7% of emulsifier and then it becomes much thicker (between 20 and 25 poises, i.e. 2 to 2.5 Pa.s).

Example 2:
Oil phase:
Glyceryl isostearate 2%
Liquid petrolatum 20%
Ethylated guar having a degree of substitution of approximately 2.5 1%
Aqueous phase:
Magnesium sulphate 0.5%
Preservatives 0.2%
Water remainder based on 100%

Example 3:
Oil phase:
Glyceryl oleate 4%
Liquid petrolatum 25%
Ethylated guar having a degree of substitution of approximately 2.5 1.5%
Aqueous phase:
4-Benzophenone (Uvinul MS40) 3%
Triethanolamine 0.8%
Water remainder based on 100%

The emulsion obtained is creamy and stable, without magnesium sulphate. It could be used in particular for protecting the skin from ultraviolet (UV) radiation.

Comparative Example 2:
Oil phase:
Glyceryl oleate 4%
Liquid petrolatum 25%
Aqueous phase:
4-Benzophenone (Uvinul MS40) 3%
Triethanolamine 0.8%
Water remainder based on 100%

The emulsion of Comparative Example 2 differs from the emulsion of Example 3 in that it does not contain gelling agent according to the invention. The emulsion is not stable to temperature cycles and to heat (such as oven at 45° C.).

Comparative Example 3:

Oil phase:

Glyceryl oleate 4%

Liquid petrolatum 25%

Aqueous phase:

4-Benzophenone (Uvinul MS40) 3%

Magnesium sulphate 1.5%

Triethanolamine 0.8%

Water remainder based on 100%

The emulsion of Comparative Example 3 differs from Example 3 in that the gelling agent according to the invention has been replaced by an electrolyte, namely magnesium sulphate.

The emulsion is stable but the Uvinul MS40 precipitates from the emulsion after storage for a few days at room temperature.

The above Examples and Comparative Examples are also described in the Priority Document, French Application No. 96-03095, which is incorporated herein by reference.

Obviously, additional modifications and variations of the present invention are possible in light of the above teachings. It is therefore to be understood that within the scope of the appended claims, the invention may be practiced otherwise than as specifically described herein.

What is claimed as new and is desired to be secured by letters patent of the United States is:

1. A water-in-oil emulsion comprising an oil phase comprising at least one gelling agent, wherein said emulsion is fluid and wherein said gelling agent is a polysaccharide alkyl ether formed from units having at least two different monosaccharide rings, each unit having at least one hydroxyl group substituted by a saturated hydrocarbon chain, wherein said emulsion is free from electrolyte or from a solid fatty substance.

2. The emulsion of claim 1, wherein said emulsion has a viscosity from 0.2 to 1.5 Pa.s.

3. The emulsion of claim 1, wherein said unit has two to four hydroxyl groups substituted by a saturated hydrocarbon alkyl chain.

4. The emulsion of claim 1, wherein said saturated hydrocarbon alkyl chain has from 1 to 24 carbon atoms.

5. The emulsion of claim 1, wherein said saturated hydrocarbon alkyl chain has from 1 to 5 carbon atoms.

6. The emulsion of claim 1, wherein said alkyl chain is selected from the group consisting of methyl, ethyl, n-propyl, isopropyl, n-butyl, isobutyl, tert-butyl chains and n-pentyl.

7. The emulsion of claim 1, wherein said monosaccharide rings are selected from the group consisting of mannose, galactose, glucose, furanose, rhamnose and arabinose.

8. The emulsion of claim 1, wherein said polysaccharide alkyl ether is an alkyl ether of a gum selected from the group consisting of guar gum, locust bean gum, karaya gum, gum tragacanth and mixtures of said gums thereof.

9. The emulsion of claim 1, wherein said polysaccharide alkyl ether has a weight average molecular weight greater than 200,000.

10. The emulsion of claim 1, wherein said polysaccharide alkyl ether is present in an amount ranging from 0.1 to 10% by weight, based on the total weight of the composition.

11. The emulsion of claim 1, wherein said polysaccharide alkyl ether is present in an amount ranging from 0.5 to 5% by weight, based on the total weight of the composition.

12. The emulsion of claim 1, wherein said emulsion is composed of a cosmetic or dermatological composition.

13. The emulsion of claim 1, wherein said emulsion contains at least one cosmetic or dermatological active ingredient for caring for or for make up of the skin or mucous membranes or for the protection against the sun of the skin or mucous membranes.

14. Process for the cosmetic or dermatological treatment of dry skin, comprising:
applying to said dry skin an effective amount of a water-in-oil emulsion, said emulsion comprising at least one gelling agent,
wherein said emulsion is fluid and wherein said gelling agent is a polysaccharide alkyl ether formed from units having at least two different monosaccharide rings, each unit containing at least one hydroxyl group substituted by a saturated hydrocarbon alkyl chain.

15. A method for stabilizing a water-in-oil emulsion, comprising adding to a fluid water-in-oil emulsion, a polysaccharide alkyl ether formed from units having at least two different monosaccharide rings, each unit having at least one hydroxyl group substituted by a saturated hydrocarbon chain, wherein said emulsion is free from electrolyte or from a solid fatty substance.

16. Process for treating a skin or a mucous membrane, comprising applying to said skin or mucous membrane an effective amount of a water-in-oil emulsion, said emulsion comprising at least one gelling agent, wherein said emulsion is fluid and wherein said gelling agent is a polysaccharide alkyl ether formed from units having at least two different monosaccharide rings, each unit having at least one hydroxyl group substituted by a saturated hydrocarbon chain, wherein said emulsion is free from electrolyte or from a solid fatty substance.

* * * * *